(12) United States Patent
Moore et al.

(10) Patent No.: US 6,251,579 B1
(45) Date of Patent: Jun. 26, 2001

(54) OXIDATIVE STABILIZATION OF COLLAGEN CONTAINING MATERIALS

(75) Inventors: Mark A. Moore, Austin; Richard E. Phillips, San Marcos; Melanie D. Robinson, Spicewood, all of TX (US)

(73) Assignee: Sulzer Carbomedics Inc., Austin, TX (US)

(*) Notice: Subject to any disclaimer, the term of this patent is extended or adjusted under 35 U.S.C. 154(b) by 0 days.

(21) Appl. No.: 09/023,549

(22) Filed: Feb. 13, 1998

(51) Int. Cl.[7] .................................................. A01N 1/02

(52) U.S. Cl. ............................. 435/1.1; 424/423; 623/2; 204/157.63

(58) Field of Search ............................ 435/1.1; 424/423; 623/2; 204/157.68

(56) References Cited

U.S. PATENT DOCUMENTS 5,412,076 * 5/1995 Gagnieu .............................. 530/356

* cited by examiner

*Primary Examiner*—Jeffrey Stucker
(74) *Attorney, Agent, or Firm*—Timothy L. Scott; Kenneth S. Barrow; Philip S. Lyren

(57) ABSTRACT

This invention relates, in general, to a process for cross-linking and stabilizing proteinaceous material, and in particular, to a process for oxidizing collagenous material, by oxidizing the tissue. The invention also relates to the resulting cross-linked product. The method comprises immersing the material to be cross-linked in a solution comprising compounds designed to generate the radical species singlet oxygen or other oxidizing intermediates without the addition of an external energy source. Immersing collagen containing tissue in a solution comprising an oxidizing agent and sufficient dissolved oxygen, under controlled conditions of pH and temperature, provides a cross-linked and stabilized collagen containing tissue that resists chemical and enzymatic degradation.

19 Claims, 2 Drawing Sheets

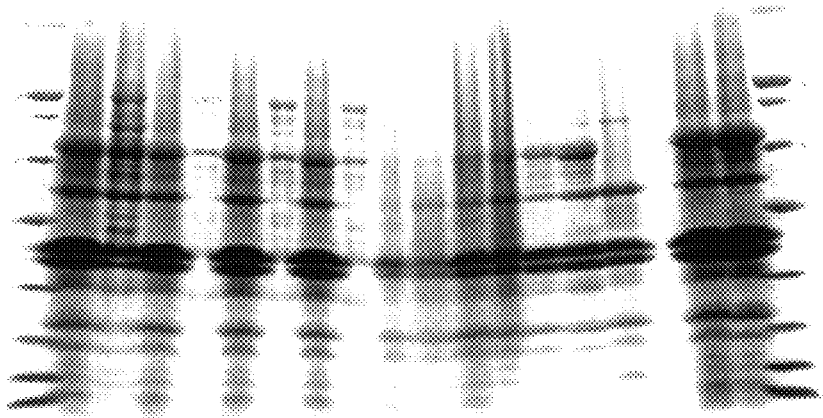

Figure 1. Digestion of tissue by CNBr, as described in Example 1. CNBr digests of 100 μM CuCl/0.37% $H_2O_2$ samples without β-mercaptoethanol pre-treatment are shown in lanes 3 and 5, and those with β-mercaptoethanol pre-treatment are shown in lanes 2 and 4. CNBr digests of 500 μM CuCl/0.37% $H_2O_2$ samples without β-mercaptoethanol pre-treatment are shown in lanes 7 and 9, and those with β-mercaptoethanol pre-treatment are shown in lanes 6 and 8. CNBr digests of ascorbate/$FeCl_3$ samples without β-mercaptoethanol pre-treatment are shown in lanes 11 and 13, and those with β-mercaptoethanol pre-treatment are shown in lanes 10 and 12. CNBr digest of $FeSO_4$ sample without β-mercaptoethanol pre-treatment is shown in lane 15, and that with β-mercaptoethanol pre-treatment is shown in lane 14. CNBr digest of photooxidized sample without β-mercaptoethanol pre-treatment is shown in lane 17, and that with β-mercaptoethanol pre-treatment is shown in lane 16. CNBr digest of untreated sample without β-mercaptoethanol pre-treatment is shown in lane 19, and that with β-mercaptoethanol pre-treatment is shown in lane 18. Broad range molecular weight standards (BioRad, Hercules, CA) are in lanes 1 and 20 and consisted of myosin (200 kDa), β-galactosidase (116 kDa), phosphorylase B (97 kDa), serum albumin (66 kDa), ovalbumin (45 kDa), carbonic anhydrase (31 kDa), and aprotinin (6.5 kDa).

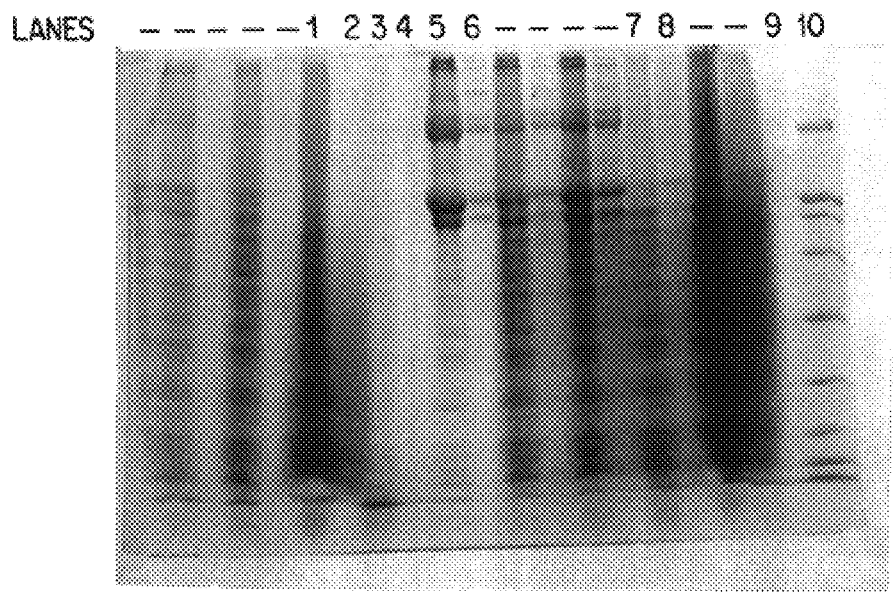

Figure 2. Digestion of tissue with pepsin digestion, as prescribed in Example 4. Pepsin digest of ascorbate/$FeCl_3$ sample is shown in lane 1, and that in 0.01 M HCl buffer only (without pepsin) in shown in lane 2. Pepsin digest of photooxidized sample is shown in lane 3, and that in 0.01 M HCl buffer only is shown in lane 4. Pepsin digest of untreated sample is shown in lane 5, and that in 0.01 M HCl buffer only is shown in lane 6. Pepsin digest of 500 µM CuCl/ 3.7% $H_2O_2$ sample is shown in lane 7, and that in 0.01 M HCl buffer only is shown in lane 8. Lane 9 is a pepsin alone sample, which contains no tissue sample. Broad range molecular weight standards (BioRad, Hercules, CA) are in lanes 1 and 20 and consisted of myosin (200 kDa), β-galactosidase (116 kDa), phosphorylase B (97 kDa), serum albumin (66 kDa), ovalbumin (45 kDa), carbonic anhydrase (31 kDa), and aprotinin (6.5 kDa).

OXIDATIVE STABILIZATION OF COLLAGEN CONTAINING MATERIALS

BACKGROUND OF THE INVENTION

1. Field of the Invention

This invention relates, in general, to a process for cross-linking and stabilizing proteinaceous material, and in particular, to a process for oxidizing collagenous material in the absence of a photo-catalyst but in the presence of chemicals that promote an oxidation reaction. The invention also relates to the resulting cross-linked product.

2. Description of the Related Art

It has been stated that degeneration of collagen and elastin are major factors in the malfunction of bioprosthestic heart valves (A. Carpentier, Biological Tissue in Heart Valve Replacement, M.I. Ionescue et al. (Eds.), Butterworth, London, 1972). Carpentier developed a method for treating the tissue to inhibit inflammatory reactions by host cells while enhancing strength and flexibility, and to prevent the degeneration of collagen and elastin. This method involved washing the tissue in an acid, i.e., in Hanks solution, then oxidizing mucopolysaccharide and glycoprotein with meta-periodate to form aldehyde groups, and finally binding and cross-linking the aldehyde groups with amines. The cross-linkages were then stabilized with sodium borohydride. This method suffered because the tissue had a tendency to calcify.

Reagents and processes currently used for protein cross-linking generally depend upon the incorporation of the cross-linking reagent into the protein matrix to cross-link the ε-amino groups of lysine hydroxylysine, and/or other groups in the protein. Common cross-linking reagents in such processes include formaldehyde and glutaraldehyde; other processes include the introduction of a phthaloyl or adipoyl moiety into the protein via phthaloyl dichloride or adipoyl dichloride, respectively, and/or the introduction of a mereaptan for oxidization to a disulfide bond. The cross-linking processes, reactions and reagents of the prior art vary, but most involve incorporating the reagent into or around the protein. For example, when collagen fibrils are cross-linked with the reagent glutaraldehyde, a polymeric-like coating forms around the fibrils, resulting in stiffer collagen matrix (Cheung and Nimni, Connec. Tissue Res. 10:201, 1982 and Connec. Tissue Res. 13:109, 1984). the incorporation of glutaraldehyde in the collagen and in the coating lead to problems such as an increased tendency of the collagen-containing tissue to calcify and a slow bleeding of the fixating agent from the tissue after it has been implanted into a host animal.

Acid has the well-known effect of denaturing the protein comprising the collagen fibril. It is, of course, the three-dimensional structure of the proteins comprising the collagen fibril which imparts to the fibril the unique properties of collagen. If there are changes to the structure of the collagen fibril, the protein cannot interact in the manner needed to give rise to those unique properties. Collagen molecules extracted by acid and neutral salt procedures differ in many respects from the natural product, including the extent to which they are covalently cross-linked, the size, shape, interaction properties and rate of fiber formation. (P. H. von Hipple, "Structural and Stabilization of the Collagen Molecule in Solution" in Treatise on Collagen, Vol. 1: Chemistry of Collagen, G. N. Ramachandran (Ed.), London: Academic Press Inc. (London) Ltd. (1967), pp. 253–338 at 262). Acid extraction does not provide collagen in a form useful for many medical applications.

A dye catalyzed process said to be useful for preparing thermostable, irreversibly cross-linked collagenous polymers is described in U.S. Pat. No. 3,152,976. This product is more susceptible to enzymatic degradation than uncross-linked collagen. Another type of dye catalyzed oxidative stabilization is described in U.S. Pat. No. 5,147,514. The tissue treated in this manner was resistant to calcification and provided material that was resistant to chemical and enzymatic degradation. However, these dyes are large and complex compounds, and there is concern about dyes remaining in the collagen bundles or tissue after treatment.

What is needed is a process that will provide cross-linked, stabilized proteinaceous products. in particular, there is a need for cross-linked, stabilized collagenous products that are suitable materials for use in the replacement and/or repair of diseased or damaged body tissues. Moreover, it is desirable that these products do not contain any foreign compounds which may later react with compounds in the host environment or leach out of the material into the host. The present invention is directed to overcoming or at least reducing the effects of one or more of the problems set forth above.

SUMMARY OF THE INVENTION

This invention relates to a process for cross-linking and stabilizing proteinaceous material, and in particular, to a process for oxidizing collagenous material. The invention also relates to the resulting cross-linked product. The process comprises immersing the proteinaceous material in a solution. The solution comprises an oxidizing agent. The oxidizing agents are those molecules that, in combination with other molecules in the solution, provide the energy to form localized reduction-oxidation reactions via a transfer of electrons. No external energy source is required. Typical oxidizing agents include (a) a mixture of copper chloride and hydrogen peroxide, (b) a mixture of ascorbate and ferrous chloride or (c) ferric sulfate. The solution usually comprises a pH buffer. At acidic pH values, below about 6.5, the acid interacts with the proteins. At lower pH values the acid will denature the protein.

The tissue remains immersed in the solution for a specified period of time at a specified temperature. While the temperature is not important, at higher temperatures the reaction proceeds at a faster rate, until heat begins denaturing the protein.

BRIEF DESCRIPTION OF THE DRAWINGS

FIG. 1 is a photo of 20 different samples, described in the specific examples, digested by cyanogen bromide/70% formic acid and analyzed by polyacrylamide gel electrophoresis. The samples were loaded on a 4–20% polyacrylamide gradient gel.

FIG. 2 is a photo of 10 different samples, described in the specific examples, digested by pepsin and analyzed by polyacrylamide gel electrophoresis.

DETAILED DESCRIPTION OF THE INVENTION

This invention relates to a process for cross-linking and stabilizing proteinaceous material, and in particular, to a process for oxidizing collagenous material. The process of the present invention provides an efficient and effective method for cross-linking and stabilizing various proteinaceous materials including, but not limited to, collagen, collagen fibrils and collagen matrices.

The term "proteinaceous material" as used herein includes both proteins such as collagen and protein-containing materials such as tissues. As a general rule, the particular proteinaceous material utilized as the starting material is determined by the intended use of the product. For instance, if it is desired to build a heart valve from the product of the process of the present invention, the preferred starting material is a material having a high collagen content such as bovine pericardium. If the cross-linked product is to be used as a vascular graft, such starting materials as the aortic arch of rats or other relatively small animals or the carotid artery of pigs, sheep, or cows are used to advantage. To make injectable collagen, finely ground reconstituted bovine skin collagen is used to advantage.

Such materials are harvested from the donor animal and immediately immersed in cold buffered saline for storage, with frequent rinses and/or changes with fresh saline, until processed in accordance with the process described herein, or solubilized or suspended if finely ground.

The invention also relates to the resulting cross-linked product. The product is resistant to enzymatic digestion, i.e. digestion by a proteolytic enzyme such as pepsin. Such resistance is evidence of cross-linking. Untreated samples, on the other hand, are readily digested by pepsin. The product is also resistant to chemical degradation. The chemically degradative agent cyanogen bromide (CNBr) in 70% formic acid was selected as the testing agent. Oxidized tissue are resistant to chemical digestion by cyanogen bromide/formic acid solutions. In contrast, untreated or control treated tissues are readily digested by these reagents. CNBr was selected in part because it provides clues as to the type of cross-linking. CNBr can specifically cleave methionyl bonds. It can not cleave these methionyl bonds, however, if they are cross-linked. β-mercaptoethanol can undo the cross-linking of methionyl bonds. When oxidized tissue is treated with β-mercaptoethanol prior to CNBr digestion, if the tissue regains susceptibility to CNBr digestion, this suggests the resistance to CNBr digestion results, at least partially, from methionine oxidation. Resistance against chemical and enzymatic degradation is evidence of cross-linking and of probable low antigenic activity in a host. Therefore, the utility of the chemical catalysts in promoting oxidative stabilization was tested by its resistance to degradation by these compounds.

This proteinaceous material should have many of the benefits of photooxidized proteinaceous material, such as having low antigenic activity and low calcification potential, but the proteinaceous material treated by the process of this invention will not have large foreign dye compounds remaining in the tissue after treatment.

The process comprises immersing the proteinaceous material in a solution. The term "immersing" as used herein includes total or partial immersion into a solution, or washing with a solution, or being dispersed or even solubilized in a solution. The makeup of the solution is not important. The solution can be water or a low ionic strength buffer, or a phosphate buffered system, or a high ionic strength buffered system, or even an organic buffer. The buffer is important because it is preferred to have a neutral or slightly alkaline system. A pH below 6.5 can result in undesired acid denaturing of the proteins.

The solution comprises an oxidizing agent. The term "oxidizing agent" are those molecules that, in combination with other molecules in the solution, provide the energy to form localized reduction-oxidation reactions that result in a transfer of electrons. No external energy source is required to generate these electrons. Typical oxidizing agents include (a) a mixture of copper chloride and hydrogen peroxide, (b) a mixture of ascorbate and ferrous chloride or (c) ferric sulfate. These oxidizing agents generally have a simple structure and can be simple salts. These oxidizing agents can therefore be readily removed from the tissue when the cross-linking reactions are complete.

Without meaning to be bound by any theory, it is thought an oxygen radical is believed to be an intermediate in the oxidation reaction. This oxygen radical, also called an oxygen singlet, is believed to be produced by a coupled oxidation-reduction reaction that consumes the oxidizing agent and cleaves dissolved oxygen molecules by electron transfer. Therefore, while the actual oxidating species may be an intermediate that is formed in solution, as used herein the term "oxidizing agent" is meant to include those compounds that are precursors to the actual oxidizing agent, or catalysts promoting the formation of intermediate radicals that are the actual oxidizing agent, or compounds that donate electrons or hydrogen atoms, or any other compounds that may participate in the oxidation reaction that results in a cross-linked product. These oxidizing reagents provide the energy to drive the reduction/oxidation reaction that directly or indirectly results in oxidation of the proteinaceous material. No external energy, in the form of light, or heat, or electrical current, need be added to the solution.

It was surprising to find that oxidation of a collagenous tissue in the presence of a chemical catalyst and sufficient oxygen, under controlled conditions of pH and temperature, made the collagenous tissue more resistant to chemical degradation and enzymatic degradation. There are many possible combinations of agents that form or promote oxygen radical formation, if indeed this is the mechanism by which the oxidation takes place. The three examples used (a) a mixture of copper chloride and hydrogen peroxide, (b) a mixture of ascorbate and ferrous chloride and (c) ferric sulfate. In each case the solution was essentially in equilibrium with the air, and therefore had dissolved oxygen present. The examples show only 3 of the almost limitless combination of chemicals that can be used to achieve the same function.

The tissue remains immersed in the solution for a specified period of time at a specified temperature. Both the temperature and the time are of limited importance. Immersion times may range from minutes to hours or even days. To a point, the longer the immersion time the greater the extent of cross-linking. The temperature of the solution is also not important. As with most catalytic or kinetic type reactions, the reaction rate increases with temperature. However, if the solution gets too warm the proteins will become denatured by the heat. In addition, the solubility, and therefore the availability, of dissolved oxygen declines with increased temperature. It is possible to oxidize proteinaceous tissue from about the freezing point of the solution used to about 40 degrees Centigrade. Higher temperatures, from about 20 degrees Centigrade to about 40 degrees Centigrade are preferred.

The following examples described the treatment procedures used for bovine pericardial tissue stabilization by active oxygen species and stability tests in detail.

EXAMPLE 1

Treatment of Bovine Pericardial Tissue with Copper Chloride and Hydrogen Peroxide and Stability Analysis by CNBr Digestion One gram of bovine pericardial tissue was immersed at 37° C. in 100 milliliters of 500 μM copper chloride ($CuCl_2$)

in 0.05 M sodium phosphate buffer, pH 7.2, for 5 minutes. Hydrogen peroxide ($H_2O_2$) was added to a final concentration of 3.7%. The tissue solution was immersed for 30 minutes. The tissue was rinsed in fresh 0.05 M sodium phosphate buffer to stop the reaction. The tissue was then transferred to 50% ethanol for storage until the tissue was tested by attempting to degrade the tissue by CNBr digestion.

Methionine oxidation can yield methionine sulphoxide, which will not react with CNBr. This reaction can be reversed by prior β-mercaptoethanol reduction, thereby restoring CNBr reactivity. Tissue samples were prepared under two different conditions, with and without β-mercaptoethanol pre-treatment. β-mercaptoethanol pre-treatment was performed in an aqueous solution comprising 25% (v:v) β-mercaptoethanol in 0.1 M ammonium carbonate at 55° C. overnight. Thiol was removed from the samples via thorough washing of tissue with 50% ethanol.

Both sets of tissue were then treated with a solution comprising CNBr and formic acid. CNBr digestions were performed in 10 mg/ml final concentration of CNBr in 70% formic acid. A 5:1 ratio of CNBr to wet weight of tissue was used. The digestion temperature was maintained at 30° C. for the entire 4 hours. Reaction aliquots were removed, diluted 10-fold with water, and lyophilized to dryness. Water addition and lyophilization were repeated twice.

The samples were then analyzed by polyacrylamide gel electrophoresis. The lyophilized samples were resuspended in water and 50 μl aliquots were separately added to 50 μl gel sample buffer. The samples were heated at 100° C. for 5 minutes and each entire 100 μl sample was loaded on a 4–20% polyacrylamide gradient gel. A photograph of the gradient gel after electrophoresis is shown in FIG. 1. Samples that were oxidized but were not subsequently treated with β-mercaptoethanol (Lanes 3, 5, 7, and 9) exhibited a resistance to CNBr digestion compared to that of untreated tissue (Lane 19). However, when $CuCl_2/H_2O_2$ oxidized samples were pre-treated with β-mercaptoethanol (Lanes 2, 4, 6, and 8) the tissue had regained susceptibility to CNBr digestion and now exhibited a banding pattern similar to that of untreated tissue (Lane 18). These results indicate that $CuCl_2/H_2O_2$ oxidative tissue treatment yields a material resistant to degradation to CNBr digestion and that oxidation is occurring at methionine residues. The lack of peptide released by CNBr digestion may be due to an extensively cross-linked matrix. Through oxidation, either a known alteration of methionine residues or the formation of a similarly cross-linked matrix would explain the resistance of this tissue to CNBr digestion.

EXAMPLE 2

Treatment of Bovine Pericardial Tissue with Ascorbate and Iron Chloride and Stability Analysis of CNBr Digestion One gram of bovine pericardial tissue was immersed at 37° C. in 100 milliliters of an aqueous solution comprising 100 millimoles (mM) magnesium chloride ($MgCl_2$) 450 mM potassium chloride (KCl), 250 mM Ascorbate, 1 mM ferric chloride ($FeCl_3$), 80 mM EDTA, and 100 mM potassium phosphate buffer, pH 6.8, for 2 hours. The tissue was rinsed in fresh 100 mM potassium phosphate buffer in order to stop the reaction. The tissue was then transferred to 50% ethanol for storage.

The tissue was then treated with CNBr and analyzed by polyacrylamide gel electrophoresis as performed in Example 1. Gel electrophoretic analysis of ascorbate/$FeCl_3$ samples without prior β-mercaptoethanol pre-treatment (FIG. 1, Lanes 11 and 13) exhibit a resistance to CNBr digestion compared to that of untreated tissue (Lane 19). When ascorbate/$FeCl_3$ oxidized samples were subsequently treated with β-mercaptoethanol (Lanes 10 and 12) the tissue had not regained susceptibility to CNBr digestion. These results indicate that ascorbate/$FeCl_3$ oxidative treatment yields a material resistant to degradation to CNBr digestion both with and without prior β-mercaptoethanol pre-treatment. This, in turn, suggests that oxidation and cross-linking is occurring at sites other than at methionine residues.

EXAMPLE 3

Treatment of Bovine Pericardial Tissue with Iron Sulfate and Stability Analysis by CNBr Digestion One gram of bovine pericardial tissue was immersed at 37° C. in 100 milliliters of an aqueous solution comprising 100 mM $MgCl_2$, 450 mM KCl, 40 mM ferrous sulfate ($FeSO_4$), and 100 mM potassium phosphate buffer, pH 6.8, for 2 hours. The tissue was then rinsed in fresh 100 mM potassium phosphate buffer to stop the reaction. Tissue was then transferred to 50% ethanol for storage.

The tissue was then treated with CNBr and analyzed by polyacrylamide gel electrophoresis as performed in Example 1. Gel electrophoretic analysis of $FeSO_4$ samples without prior β-mercaptoethanol (FIG. 1, Lane 15) exhibit a resistance to CNBr digestion compared to that of untreated tissue (Lane 19). When $FeSO_4$ oxidized samples were subsequently treated with β-mercaptoethanol (Lane 14) the tissue had not regained susceptibility to CNBr digestion. These results indicated that $FeSO_4$ oxidative tissue treatment yields a material resistant to degradation to CNBr digestion both with and without prior β-mercaptoethanol pre-treatment.

EXAMPLE 4

Treatment of Bovine Pericardial Tissue with Copper Chloride and Hydrogen Peroxide and Stability Analysis by Pepsin Digestion Treatment of bovine pericardial tissue with $CuCl_2/H_2O_2$ was performed as stated in Example 1. The $CuCl_2/H_2O_2$ treated tissue was subjected to pepsin digestion and analyzed by polyacrylamide gel electrophoresis. Tissue samples were digested in 0.04 mg/ml pepsin in 0.01 M HCl for 4 hours at 37° C. The enzyme to tissue ratios, on a weight to wet weight basis, was 1:2,500. Following centrifugation at 4° C. for 2 hours at 14,000 rpm, reaction supernatants were retained for gel electrophoresis. A 50 μl aliquot was added to 50 μl of gel sample buffer. The samples were heated at 100° C. for 5 minutes and the entire 100 μl sample was loaded on a 4–20% gradient gel. Gel electrophoretic analysis of pepsin reaction solutions (FIG. 2, Lane 7) indicates that the $CuCl_2/H_2O_2$ oxidative tissue treatment yields a material resistant to degradation by pepsin digestion compared to that of untreated tissue (Lane 5). The lack of protein in extraction samples is attributed to a resistance to protein extraction imparted by oxidation. The buffer control samples (Lanes 6 and 8) consisted of tissue immersed in the buffer alone, in the absence of pepsin. The pepsin-only control sample (Lane 9) consisted of the same quantity of enzyme immersed as above, but in the absence of tissue.

EXAMPLE 5

Treatment of Bovine Pericardial Tissue with Ascorbate and Iron Chloride and Stability Analysis by Pepsin Digestion Treatment of bovine pericardial tissue with ascorbate and $FeCl_3$ was performed as stated in Example 2. The ascorbate/

FeCl₃ treated tissue was subjected to pepsin digestion and analyzed by polyacrylamide gel electrophoresis as stated in Example 4. Gel electrophoretic analysis of pepsin reaction solutions (FIG. 2, Lane 1) indicated that ascorbate FeCl₃ oxidative tissue treatment yields a material which liberates less intact collagen upon treatment by pepsin compared to that of untreated tissue (Lane 5). The lack of protein in extraction samples is attributed to a resistance to protein extraction imparted by oxidation. The buffer control samples (Lanes 2 and 6) consisted of tissue immersed in the buffer alone, in the absence of pepsin.

These examples demonstrate that oxidative treatment of collagen containing samples can yield materials which are stable to chemical and proteolytic degradation. The stability of these materials to degradation is desirable for particular medical applications.

What is claimed is:

1. The process of producing an oxidized, stabilized collagenous tissue comprising immersing the tissue into a solution comprising an oxidizing agent or agents.

2. The process of claim 1 wherein the solution comprises dissolved oxygen and the oxidizing agent or agents comprise elements or compounds designed to generate the active species singlet oxygen.

3. The process of claim 1 wherein the oxidizing agents comprise copper chloride and hydrogen peroxide.

4. The process of claim 1 wherein the oxidizing agents comprise ascorbate and ferrous chloride.

5. The process of claim 1 wherein the oxidizing agent or agents comprises ferric sulfate.

6. The process of claim 2 wherein the process comprises immersing the tissue to copper chloride in a buffered saline solution for at least about 1 minute, and then adding hydrogen peroxide to the solution, and then immersing the tissue for at least 5 minutes.

7. The process of claim 6 wherein the solution comprises between about 0.05 millimoles per liter and about 50 millimoles per liter copper chloride buffered to a pH from about 6.5 to about 8, and the tissue is immersed in solution comprising copper chloride from about 1 minute to about 60 minutes at a temperature from about 1° to about 40° C., and then the quantity of hydrogen peroxide added is sufficient to give a concentration from about 0.1% to about 6%, and the tissue is immersed in this resulting solution from about 10 minutes to about 12 hours at a temperature from about 1° to about 40° C.

8. The process of claim 6 wherein the solution comprises between about 0.5 millimoles per liter and about 10 millimoles per liter of copper chloride and a phosphate buffer which maintains the pH from about 6.5 to about 8, and the tissue is immersed for a period of time from about 1 minute to about 30 minutes at a temperature from about 15° to about 40° C., and then the quantity of hydrogen peroxide is sufficient to give a concentration from about 0.2% to about 6%, and the tissue is immersed in this resulting solution from about 10 minutes to about 12 hours at a temperature from about 1° to about 40° C.

9. The process of claim 6 wherein the solution comprises between about 1 millimole per liter and about 5 millimoles per liter copper chloride and a phosphate buffer which maintains the pH from about 6.5 to about 7.5, and the tissue is immersed from about 2 minute to about 30 minutes at a temperature from about 15° to about 40° C., and then the quantity of hydrogen peroxide added is sufficient to give a concentration from about 0.2% to about 6%, and the tissue is immersed in this resulting solution from about 20 minutes to about 4 hours at a temperature from about 15° to about 40° C.

10. The process of claim 4 wherein the solution comprises between about 100 millimoles per liter and about 50000 millimoles per liter ascorbate and between about 0.5 millimoles per liter and about 200 millimoles per liter ferric chloride, buffered to between about pH 6.5 and about pH 8, and the tissue is immersed for between about 5 minutes and about 12 hours.

11. The process of claim 4 wherein solution comprises between about 1000 millimoles per liter and about 5000 millimoles per liter ascorbate and between about 1 millimoles per liter and about 50 millimoles per liter ferric chloride, buffered to between about pH 6.5 and pH 7.5, and the tissue is immersed for between about 10 minutes and about 6 hours at a temperature from about 15° to about 40° C.

12. The process of claim 4 wherein the solution comprises between about 1000 millimoles per liter and about 5000 millimoles per liter ascorbate, between about 10 millimoles per liter and about 1000 millimoles per liter ferric chloride, between about 100 millimoles per liter and about 2000 millimoles per liter magnesium chloride, and between about 100 millimoles per liter and about 2000 millimoles per liter potassium chloride, buffered to between about pH 6.5 and pH 7.5, and the tissue is immersed for between about 10 minutes and about 4 hours at a temperature from about 15° and about 40° C.

13. The process of claim 5 wherein the solution comprises between about 10 millimoles per liter and about 3000 millimoles per liter ferrous sulfate, buffered to between about pH 6.5 and about pH 8, and the tissue is immersed for between about 5 minutes and about 12 hours at a temperature from about 1° and about 40° C.

14. The process of claim 5 wherein the solution comprises between about 50 millimoles per liter and about 1000 millimoles per liter ferrous sulfate, buffered to between about pH 6.5 and about pH 7.5, and the tissue is immersed for between about 10 minutes and about 6 hours at a temperature from about 15° and about 40° C.

15. The process of claim 5 wherein the solution comprises between about 200 millimoles per liter and about 800 millimoles per liter ferrous sulfate, between about 100 millimoles per liter and about 2000 millimoles per liter magnesium chloride, and between about 100 millimoles per liter and about 2000 millimoles per liter potassium chloride, buffered to between about pH 6.5 and about pH 7.5, and the tissue is immersed for between about 30 minutes and about 4 hours at a temperature from about 15° and about 40° C.

16. The product of the process of claim 1.
17. The product of the process of claim 3.
18. The product of the process of claim 4.
19. The product of the process of claim 5.

* * * * *